US00PP28204P2

(12) United States Plant Patent
Hansen

(10) Patent No.: US PP28,204 P2
(45) Date of Patent: Jul. 18, 2017

(54) ***BUDDLEIA* PLANT NAMED 'LITTLE ANGEL'**

(50) Latin Name: ***Buddleia* hybrid**
Varietal Denomination: Little Angel

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 14/999,590

(22) Filed: May 31, 2016

(51) Int. Cl.
*A01H 5/00* (2006.01)

(52) U.S. Cl.
USPC ..... Plt./242

(58) Field of Classification Search
USPC ..... Plt./242
See application file for complete search history.

*Primary Examiner* — Annette Para

(57) ABSTRACT

*Buddleia* 'Little Angel' is a short, compact, dense, round-mounded, multi-stemmed, winter-hardy butterfly bush with long, compact, flowering, thyrse starting early and over a long season beginning mid-summer and continuing until frost, from soil line to top of plant, with sweetly-fragrant flowers with yellow-orange throat that are attractively offset by dark green foliage with silvery undersides.

1 Drawing Sheet

Botanical classification: *Buddleia* hybrid.
Variety denomination: 'Little Angel'.

BACKGROUND OF THE PLANT

The present invention relates to the new and distinct butterfly bush plant of the Scrophulariaceae family, *Buddleia* 'Little Angel' hybridized by Hans A. Hansen in the summer of 2010 at a wholesale perennial nursery in Zeeland, Mich., USA. 'Little Angel' is the result of an ongoing breeding program conducted by the inventor. The goals for this program have been to produce improved, garden-worthy plants for the ornamental plant market. Seeds from a cross of *Buddleia* 'Blue Chip' U.S. Plant Pat. No. 19,991 as the female or seed patent and *Buddleia* 'Podaras #8' U.S. Plant Pat. No. 22,069 as the male parent were harvested on Aug. 8, 2010. The selection was of a single seedling initially selected in the summer of 2011 and assigned breeder code H10-23-01.

No plants of *Buddleia* 'Little Angel' have been sold, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

*Buddleia* 'Little Angel' was first asexually propagated from the single select plant in 2012 by stem cuttings at the same nursery in Zeeland, Mich. The resultant asexually propagated plants have been found to be stable and true to type in successive generations of asexual reproduction.

SUMMARY OF THE INVENTION

Plants of the new *Buddleia* have not been observed under all possible environmental conditions. The phenotype may vary somewhat with variations in environment and cultural practices such as temperature, light intensity, available moisture and fertility without, however, any variance in genotype.

There are other white to creamy-white-flowering cultivars of *Buddleia* known to the inventor including: 'Morning Mist' U.S. Plant Pat. No. 17,332, 'Podaras #1' U.S. Plant Pat. No. 22,080, 'Podaras #15' U.S. Plant Pat. No. 22,143 and 'Ice Chip' U.S. Plant Pat. No. 24,015. Both 'Podaras #1' and 'Podaras #15' have upright and spreading habits. 'Morning Mist' is much taller and broader in habit than 'Little Angel'. Compared to 'Podaras #1' the new plant has an inflorescence that is nearly three times as long. Compared to 'Podaras #15' the new plant is more compact and rounded in habit and not the upright spreading habit of 'Podaras #15' and the new plant has well over ten times the number of flowers and buds per inflorescence. Compared to 'Ice Chip' the new plant produces a long thin densely flowered thyrse, and 'Ice Chip' produces a shorter lose panicle.

The new plant has pure white flowers compared to the two parents which both produce blue to lavender flowers.

*Buddleia* 'Little Angel' is a unique winter-hardy butterfly bush different from all other *Buddleia* cultivars known to the inventor based on the following combined traits:

1. Winter-hardy shrub, with multiple-stemmed, branched, compact, dense, round-mounded habit.
2. Many-flowered, long, narrow thyrse starting early and over a prolonged season beginning mid-summer and continuing to frost from soil line to top of plant.
3. Self-cleaning, pure-white fragrant flowers with yellow-orange throat.
4. Lanceolate foliage of dark green with silvery undersides.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
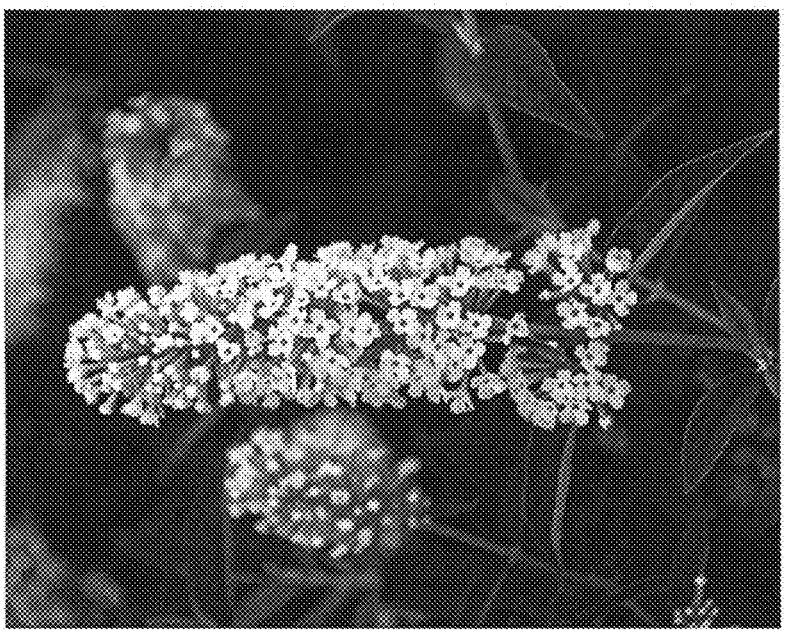
FIG. 1 shows a close-up of the flowers and buds.
Figure 2:
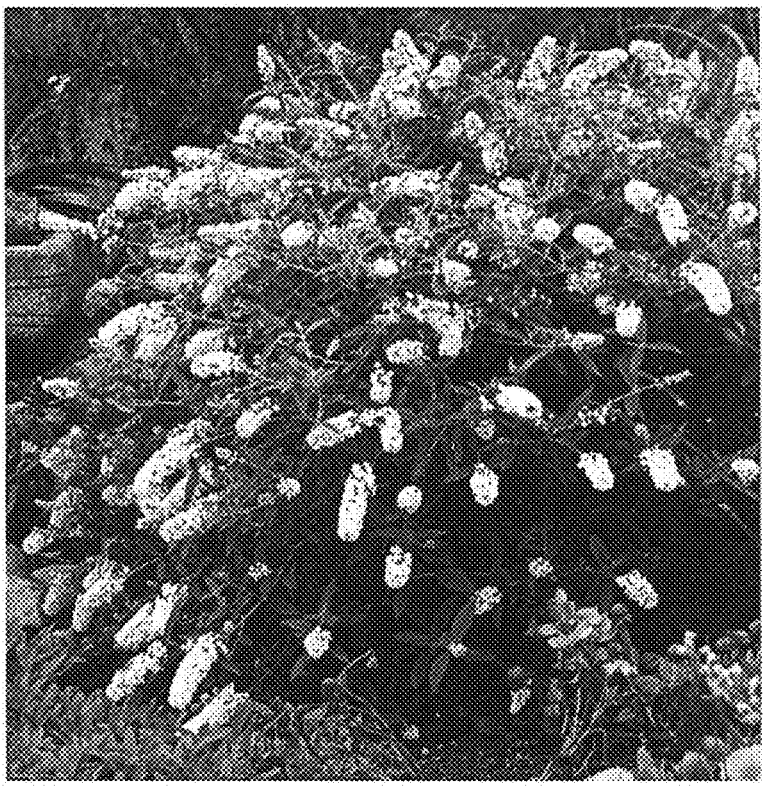
FIG. 2 shows the habit of a three-year-old plant in mid-season flowering.

The following descriptions and color references are based on the 2001 edition of The Royal Horticultural Society Colour Chart except where common dictionary terms are used. The new plant, *Buddleia* 'Little Angel', has not been observed under all possible environments. The phenotype may vary slightly with different environmental conditions, such as temperature, light, fertility, moisture and maturity levels, but without any change in the genotype. The following observations and size descriptions are of two-year-old plants in the loamy-sand, open-sun, field trials of a nursery in Zeeland, Mich. with supplemental fertilizer and water as needed. The plants are natural habit and were not treated with plant growth regulators, nor were they pinched at any time in the growth year except to cut back woody stems to about 15 cm tall in fall or early spring to promote new growth and flowering.

Parentage: 'Blue Chip' as the female or pod parent times and 'Podaras #8' as the male or pollen parent;

Propagation:

*Method*.—Softwood cuttings.

*Time to initiate roots from tissue culture*.—About two weeks.

*Rooting habit*.—Normal, dense and thick at base to about 1.5 cm diameter; fibrous, branching.

*Root color*.—Creamy white between RHS 159A and lighter than RHS 159 D depending on soil type.

*Crop time*.—Under normal spring growing conditions 6 to 7 weeks to fill and flower in a four-liter container a 65 mm liner; 8-10 weeks to finish and flower in a four-liter container from a 25 mm liner; Plant vigor is very good.

Plant description:

*Plant shape and habit*.—Winter-hardy, semi-woody, well-branched, low mounded habit with about 9 thick upright and branched main stems producing a compact rounded mound about 90 cm tall and about 140 cm wide.

*Stem*.—Terete and woody in lower portion with slightly exfoliating bark; younger upper portion puberulent and quadrangular in cross section with ridges in corners; strong and flexible; basal about 30.0 cm becoming woody and rigid; average about 80 cm long from soil line to just below terminal flowers, and about 8.0 to 10.0 mm diameter average about 9.0 mm diameter at the base; before distal flowers about 10 branches per main stem; attitude outward to slightly drooping toward inflorescence.

*Stem color*.—Distal portion just below peduncles between RHS 145C and RHS 145B, and in about basal 10 cm alternating striations of nearest RHS 199A with striations nearest RHS 161D; woody stems about 4.0 mm diameter and about 30.0 cm above soil nearest RHS 199D.

*Plant size*.—Unpinched plant with stems flowering to about 90.0 cm tall; overall plant about 140.0 cm wide.

*Internode*.—About 12 nodes per stem below flowers, average internode length about 6.0 cm on unpinched plant; upper internodes slightly more elongated than lower internodes.

Foliage description: Opposite, decussate; serrulate; puberulent adaxial and canescent to tomentose adaxial; lanceolate with attenuate base and sharply acute apex; no foliar fragrance detected;

*Leaf blade size*.—Up to about 8.0 cm long and about 3.0 cm wide, average about 6.4 cm long and about 2.3 cm wide; becoming smaller in distal portion of stem.

*Foliage color*.—Young expanding leaf adaxial side between RHS N138B and RHS N138C, young expanding abaxial nearest RHS 192D; mature leaves adaxial side between RHS 147A and RHS 139A, and abaxial between RHS 189C and RHS 189B.

*Veins*.—Reticulate; abaxial raised, adaxial slightly impressed.

*Vein color*.—Young expanding adaxial midrib nearest RHS 192C and lateral veins between RHS N138B and RHS N138C, abaxial young expanding midrib nearest RHS 145D, lateral veins nearest RHS 192D; mature adaxial midrib nearest RHS 145D lateral veins between RHS 147A and RHS 139A; abaxial midrib and lateral vein blend between RHS 145C and RHS 145D and RHS 193 B and RHS 193C.

*Petioles*.—Glaucous and tomentose to pubescent adaxial and abaxial; flatted partially top to bottom; average size about 5.0 mm long and about 1.0 mm wide at base.

*Petiole color*.—Nearest RHS 193C adaxial and abaxial.

*Inflorescence description*.—Glomerate thyrse consisting of about 900 self-cleaning salverform flowers; to about 29.5 cm long and about 4.7 cm across; beginning in mid-July and continuing until late October in Michigan; attitude outward to slightly drooping.

*Flowers fragrance*.—Pleasantly and distinctly sweet.

*Flower attitude*.—Upward and outward.

*Lastingness of inflorescence*.—About 10 to 14 days.

*Lastingness of individual flower*.—About 3 to 5 days.

*Buds*.—Elongated clavate with straight tube, apex rounded; one day prior to opening about 8.0 mm long and about 2.0 mm diameter in club and throat about 1.0 mm diameter in throat and about 7.0 mm long.

*Bud color*.—Nearest RHS 155D in club portion and tube portion nearest RHS 170D.

*Sepals*.—Typically four, proximal two-thirds connate, adpressed to corolla tube; acute apex; glabrous adaxial and pubescent abaxial; margin entire, edentate; fused in about the basal 1.6 mm and split in about the terminal 0.9 mm; forming a corolla about 2.5 mm long and about 1.0 mm across; individually less than about 1.0 mm wide at point of fusion.

*Sepal color*.—Adaxial nearest RHS 138C, abaxial nearest RHS 145A.

*Petals*.—Four; glabrous; fused into salverform with typically straight cylindrical tube about 8.0 mm long and 1.0 mm diameter, and a flattened face about 6.0 mm across; petal blade rounded with crenate margin; blade to about 2.4 mm across and about 2.2 mm long from fused face.

*Petal color*.—Adaxial tube center between RHS 23B and RHS 23A with a thin irregular band in the center face of less than 0.5 mm width of between RHS 18B and RHS 18A, adaxial face blades white, lighter than RHS 155D; abaxial tube between RHS 35D and RHS 35C and abaxial petal blades white, lighter than RHS 155D.

*Gynoecium*.—Pistil: one; about 3.5 mm long. Style: short, round, glabrous; about 1.5 mm long and less than 0.2 mm diameter; color nearest RHS 144C. Stigma: oblong, minutely puberulent; about 0.4 mm in diameter and less than 0.5 mm long; color nearest RHS 144B. Ovary: superior; oblong; about 1.0 mm across at base and 1.5 mm tall; distally tapering to style; color between RHS 144A and RHS 144B.

*Androecium*.—Filaments: not produced or very short. Anthers: typically four; oblong; introrse; adnate to about mid-point of corolla tube; about 1.0 mm long and 0.5 mm wide; color nearest RHS 165A. Pollen: numerous, globose, less than 0.1 mm long; color nearest RHS 4D.

*Pedicel*.—Short, puberulent; about 2.0 mm long and about 0.5 mm diameter; color nearest than RHS 138B.

*Peduncle*.—Quadrangular, pubescent, flexible and strong; flowering portion to about 27.5 cm long.

*Peduncle color*.—Nearest RHS 138B.

*Fruit and seed*.—Have not yet been observed.

Disease resistance: Resistance has been noted to deer browsing. Other resistance beyond that of known butterfly bush cultivars has not been observed. The plant grows best with plenty of moisture and adequate drainage, but is able to tolerate some drought when mature. Hardiness at least from USDA zone 6 through 10.

I claim:

1. A new cultivar of winter-hardy butterfly bush *Buddleia* plant named 'Little Angel' as herein illustrated and described, especially suitable for potted plant culture, landscaping as a specimen or en masse or as cut flower purposes.

* * * * *